(12) United States Patent
Wang et al.

(10) Patent No.: US 7,605,278 B2
(45) Date of Patent: Oct. 20, 2009

(54) METHODS AND COMPOSITIONS FOR CONVERTING TAXANE AMIDES TO PACLITAXEL OR OTHER TAXANES

(75) Inventors: Dasheng Wang, Dublin, OH (US); Rex T. Gallagher, Hampton, NH (US); John S. Juchum, Gloucester, MA (US); James H. Johnson, Merrimac, MA (US)

(73) Assignee: Natural Pharmaceuticals, Inc., Beverly, MA (US)

( * ) Notice: Subject to any disclaimer, the term of this patent is extended or adjusted under 35 U.S.C. 154(b) by 363 days.

(21) Appl. No.: 10/522,696

(22) PCT Filed: Aug. 4, 2003
(Under 37 CFR 1.47)

(86) PCT No.: PCT/US03/24666

§ 371 (c)(1),
(2), (4) Date: May 30, 2006

(87) PCT Pub. No.: WO2004/013096

PCT Pub. Date: Feb. 12, 2004

(65) Prior Publication Data

US 2008/0051589 A1    Feb. 28, 2008

Related U.S. Application Data

(60) Provisional application No. 60/401,191, filed on Aug. 4, 2002.

(51) Int. Cl.
*C07D 305/14* (2006.01)
*C07D 493/00* (2006.01)

(52) U.S. Cl. ...................... 549/510; 549/511

(58) Field of Classification Search .............. 549/510, 549/511
See application file for complete search history.

(56) References Cited

U.S. PATENT DOCUMENTS

| | | | |
|---|---|---|---|
| 5,319,112 A | 6/1994 | Kingston et al. | |
| 5,677,470 A | 10/1997 | Tsujihara et al. | |
| 5,679,807 A | 10/1997 | Murray et al. | |
| 5,808,113 A | 9/1998 | Murray et al. | |
| 6,028,206 A * | 2/2000 | Chattopadhyay et al. | 549/510 |
| 6,358,996 B1 | 3/2002 | Alexander et al. | |
| 6,448,417 B1 | 9/2002 | Sisti et al. | |
| 6,479,679 B1 | 11/2002 | Zygmunt et al. | |
| 7,220,872 B2 * | 5/2007 | Johnson et al. | 549/511 |

FOREIGN PATENT DOCUMENTS

| | | |
|---|---|---|
| WO | WO-94/14787 A1 | 7/1994 |
| WO | WO-96/23780 A1 | 8/1996 |
| WO | WO-00/69840 A1 | 11/2000 |

* cited by examiner

*Primary Examiner*—Janet L. Andres
*Assistant Examiner*—Raymond Covington
(74) *Attorney, Agent, or Firm*—Alston & Bird LLP

(57) ABSTRACT

The invention relates to methods and compositions for converting taxane amides to paclitaxel or other taxanes. In one alternative embodiment, the present invention comprises; (i) selectively protecting at least one OH group of a taxane amide; (ii) contacting the taxane amide with a transition metal compound to reduce the amide; (iii) contacting the reduced amide with an agent capable of substantially removing the transition metal; (iv) contacting the reduced amide with a hydrolyzing amount of acid to form a taxane amine salt in solution; (v) adding a sufficient amount of solvent to solidify the amine salt; and (vi) converting the taxane amine salt into paclitaxel or other taxanes.

36 Claims, 11 Drawing Sheets

P = H or protecting group

P = H or protecting group

Taxol A
(Paclitaxel)

Taxol B
(Cephalomannine)

Taxol C

Taxol D

Taxol E

Taxol F

Taxol G

Docetaxel

FIGURE 16 cont'
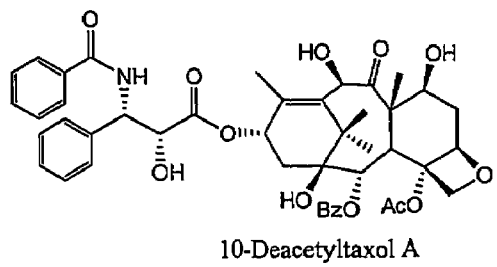
10-Deacetyltaxol A
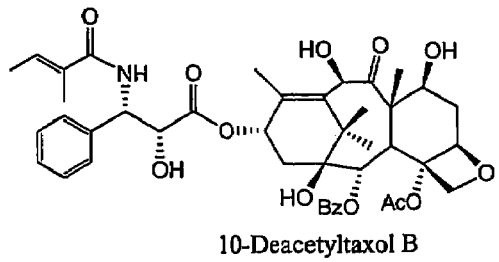
10-Deacetyltaxol B
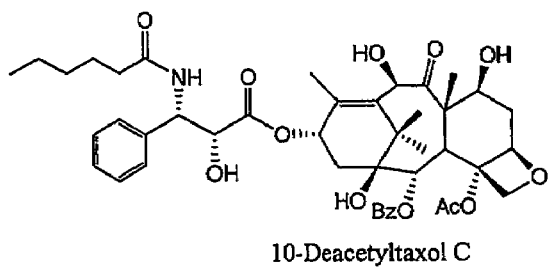
10-Deacetyltaxol C
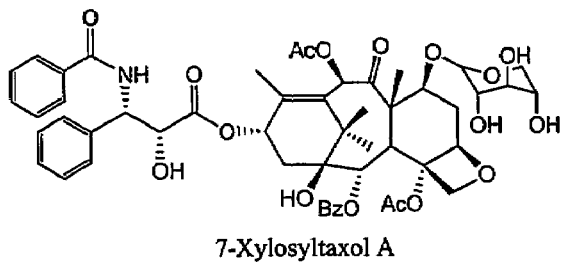
7-Xylosyltaxol A
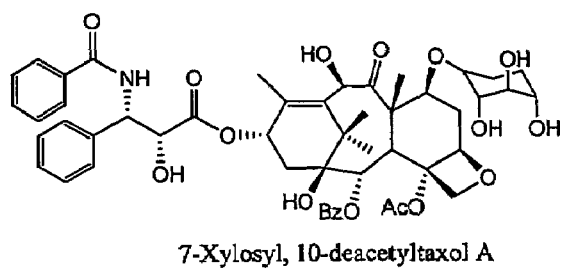
7-Xylosyl, 10-deacetyltaxol A
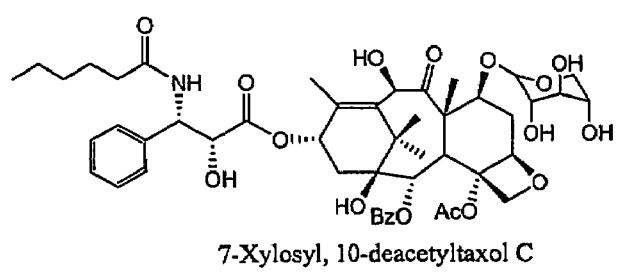
7-Xylosyl, 10-deacetyltaxol C Bis(monomethylcyclopentadienyl)
zirconium chloride hydride Bis(pentamethylcyclopentadienyl)
zirconium chloride hydride Bis(cyclopentadienyl)
zirconium methylsufonate hydride Bis(cyclopentadienyl)
zirconium triflate hydride Bis(cyclopentadienyl)
hafnium chloride hydride Bis(cyclopentadienyl)
titanium chloride hydride ated Applications This application claims priority from U.S. Provisional Application Ser. No. 60/401,191, filed Aug. 4, 2002. This application is incorporated herein by reference in its entirety.

METHODS AND COMPOSITIONS FOR CONVERTING TAXANE AMIDES TO PACLITAXEL OR OTHER TAXANES

CROSS REFERENCE TO RELATED APPLICATIONS

This application claims priority from U.S. Provisional Application Ser. No. 60/401,191, filed Aug. 4, 2002. This application is incorporated herein by reference in its entirety.

I. FIELD OF INVENTION

The invention relates to novel processes and compositions for converting taxane amides to paclitaxel or other taxanes. The process of this invention also provides new taxane compounds that are useful in the production of taxanes.

II. BACKGROUND OF THE INVENTION

Taxanes, such as paclitaxel, and other compounds derived from biomass or semi-synthetically have been identified as having significant anticancer properties. Because of the promising clinical activity of certain taxanes (e.g., paclitaxel) against various types of cancer, there is an ongoing need for different methods for preparing paclitaxel and other taxane molecules, including paclitaxel derivatives and analogues. It is believed that the preparation of paclitaxel derivatives and analogues may result in the synthesis of compounds with comparable or greater potency, superior bioavailability, and/or fewer side effects than paclitaxel. Interconversion of one taxane molecule or mixtures of taxane molecules into another taxane molecule is one route to provide various paclitaxel derivatives and analogues for further study of their biological properties.

In addition, the supply and cost of obtaining paclitaxel and other taxane molecules has always been a concern. Three general methods exist for producing paclitaxel. The first is by isolating natural paclitaxel from a biomass source such as Taxus species or from various fermentation broths. The second is by semi-synthesis starting from a related natural taxane compound, and the third is by total synthesis. Only the first two methods are economically viable. The second method can further be divided into multiple approaches depending on the starting taxane compound. In any case, an improved method of producing paclitaxel or other taxanes is of high importance Murray et al. describe a process for converting taxol A, taxol B, and taxol C to taxol A or docetaxel (U.S. Pat. Nos. 5,679,807 and 5,808,113). The process generally includes reductive deoxygenation of the C-3' amide group of a fully protected taxane molecule using Schwartz's reagent to form an imine, followed by hydrolysis of the imine to a primary amine. Subsequent acylation of the primary amine with benzoyl chloride or tert-butyloxycarbonyl anhydride can produce taxol A or docetaxel, respectively.

In another example, Kingston et al. describe the conversion of taxol B into paclitaxel by substituting the 2-methyl-2-butenoyl group on the C-13 side chain of taxol B with a benzoyl group (U.S. Pat. No. 5,319,112). The methodology generally includes in sequential order: hydrogenation of the 2-methyl-2-butenoyl group, benzoylation of the C-2' hydroxyl group, protection of the C-7 hydroxyl group as its trichloroethyloxycarbonyl group, reaction of the C-3' amide functionality with oxalyl chloride followed by addition of water, reaction with diphenylcarbodiimide to create a free amine at the C-3' position followed by acyl migration of the benzoyl group from the C-2' hydroxyl group, and removal of the trichloroethyloxycarbonyl group.

In yet another example, International Application Serial No. PCT/US03/10557 entitled "Conversion of Taxane Molecules," filed Apr. 5, 2003, describes methods and compositions for reductively deoxygenating an amide group at a C-3' position of a taxane molecule followed by migration of an acyl group from C-2' to the C-3' position. Such methods generally includes the steps of acylating the 2' hydroxyl; reductively deoxygenating the taxane molecules to form an imine compound; hydrolyzing the imine compound to form a primary amine compound; and then contacting primary amine compound with a base to effect acyl migration.

Thus, there is still a need for other synthetic methodologies for converting taxane molecules into other taxane molecules, which may be more potent anti-cancer compounds. There is also a need for chemical compounds, including taxane molecules, analogs and their intermediates that are useful in the production of paclitaxel or other taxanes.

Accordingly, the present invention is directed to an improved method of converting taxane amides to paclitaxel or other taxanes including, but not limited to, those taxanes listed in FIG. 16. The process of this invention also produces new taxane intermediate compounds, including, but not limited to, taxane amine sulfate salts, that are useful in the production of taxanes.

III. SUMMARY OF THE INVENTION

In one embodiment, the invention provides a method of converting a taxane molecule into a taxane amide having the formula shown in FIG. 1, where $R_1$ is hydrogen; $R_2$ is hydrogen, an acyl group or a hydroxyl protecting group; $R_4$ is a acetate group; $R_7$ is hydrogen, an alkyl group, an aryl group, an ester group, an ether group, a glycoside group, an oxo-group, or a hydroxyl protecting group; $R_{10}$ is hydrogen, an alkyl group, an aryl group, an ester group, an ether group, or a hydroxyl protecting group; $R_2'$ is a hydrogen, a hydroxyl-protecting group, an alkyl group, an aryl group, an ester, an ether group, or a vinyl group; $R_N$ is a hydrogen or an alkyl group; $R_{AC}$ is an alkoxy group, an alkyl group, an aryl group, an arylalkyl group, an ether group, a heterocyclic group, an acyl group, or a vinyl group; to another taxane molecule having the formula shown in FIG. 2, where $R_1$, $R_2$, $R_4$, $R_7$, $R_{10}$, $R_2'$, $R_N$, and $R_{AC}$ are as defined above.

The preferred $R_{AC}$ groups are those of known taxane compounds and derivatives thereof, e.g., phenyl, 1-methyl-1-propenyl, n-pentyl, n-propyl, 1-methylpropyl, benzyl, 2-furanyl, and tert-butoxy. In addition, preferred taxane compounds including those having the above-illustrated formula, where $R_1$ is hydrogen; $R_2$ is a benzoyl group; $R_4$ is an acetate; $R_7$ is hydrogen; $R_{10}$ is hydrogen or an acetate group; and $R_N$ is hydrogen.

The method generally includes one or more of the following steps: (i) reductively deoxygenating the taxane amide compound or mixture of taxane amide compounds, with or without hydroxyl group protection, to form an imine compound;(ii) hydrolyzing the imine compound to form a taxane amine salt; and (iii) reacting the amino group of the amine to form a new or single taxane amide compounds. Preferably, the conversion of the taxane molecule occurs without isolation of one or more of the intermediates, i.e., the imine compound and the taxane amine salt, thereby providing an efficient, cost effective synthetic methodology for producing paclitaxel or other taxanes.

In one alternative embodiment, the reductive deoxygenation preferably is carried out using a zirconium hydride compound such as zirconocene chloride hydride (bis(cyclopentadienyl)zirconium chloride hydride), commonly known as Schwartz's reagent. Preferably, about 3 or more molar equivalents of zirconocene chloride hydride are used and/or the reaction temperature is maintained at less than about 15° C.

In one alternative embodiment, the present invention is directed to a process for converting taxanes containing an amide functional group to paclitaxel or other taxane molecules. In one alternative embodiment, the present invention is carried out by first contacting at least one OH protected or unprotected taxane or mixture of taxanes comprising an amide functional group in a first solvent, preferably tetrahydrofuran, with a reductive deoxygenating amount of a transition metal reducing agent, preferably zirconocene chloride hydride (Schwartz's reagent). This reaction yields an OH protected or unprotected imine. Substantial amounts of zirconium salts remaining in solution may be removed by contacting the solution with an appropriate amount of chelating agent, preferably bicine. Other chelating agents, such as EDTA, nitriloatriacetic acid, and Tiron® may also be used.

The resulting imine is then hydrolyzed by contacting it with a hydrolyzing amount of an acid, preferably sulfuric acid, to yield a taxane amine salt. This salt may be solidified by adding an appropriate amount of a second, less polar solvent or anti-solvent, preferably methyl tert-butyl ether. As used herein, the term "less polar solvent" or "anti-solvent" means a solvent less polar than that used in converting the taxane amide to a taxane imine. Other less polar solvents, such as dichloromethane, heptane, hexane, toluene or trifluorotoluene may also be used.

The solidification step serves to purify the taxane amine salt in that substantially all the neutral compounds and other impurities in the reaction mixture remain in solution. The taxane amine may be converted into paclitaxel or other taxanes by contacting it with a benzoylating agent, preferably benzoyl chloride. Suitable benzoylating agents are described in U.S. Patent Application Publication No. 2006/0035962, which is the publication of U.S. application Ser. No. 11/196, 950, which claims priority to U.S. application Ser. No. 60/444,847, filed Feb. 4, 2003. The noted publication is incorporated herein by reference in its entirety.

In one alternative embodiment, the processes of the present invention may provide substantially purified taxanes. In an alternative embodiment, the resulting taxane may be at least 70% pure, 70% to 90% pure, 75% to 95% pure, or 90% to 95% pure. If desired, the resulting taxane may be purified further by other means known in the art.

The foregoing, and other features and advantages of the invention will be understood from the description, figures, and claims which follow.

IV. DESCRIPTION OF THE DRAWINGS

V. DETAILED DESCRIPTION OF THE INVENTION

Figure 1:
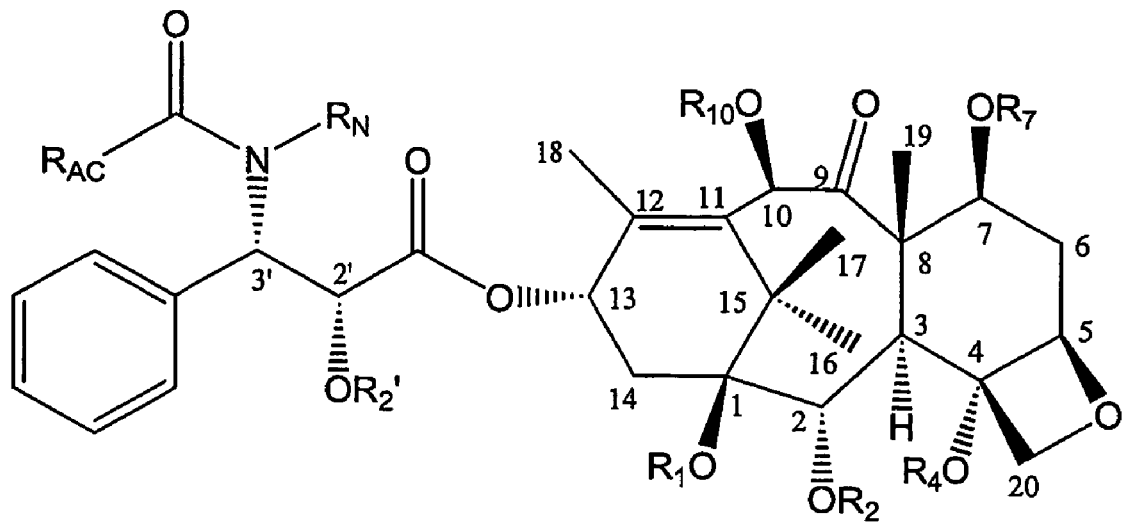
FIG. 1 shows a non-limiting, exemplary taxane for use in the present invention.

The invention is based, in part, on the discovery of an efficient synthetic route for the interconversion of taxane molecules that may be realized using reductive deoxygenation, hydrolysis and acylation. In particular, the method of the invention has utility in transforming mixtures of taxane molecules into one specific taxane molecule.

As used herein, an "alkoxy group" means a linear, branched, or cyclic saturated hydrocarbon attached to an oxygen atom. Preferably, an alkoxy group has between one and six carbon atoms. An alkoxy group also refers to substituted alkoxy groups, which may include substituents such as alkanoyloxy groups, alkenyl groups, alkyl groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred examples of alkoxy groups include, among others, methoxy, ethoxy, propoxy, cyclopropoxy, isopropoxy, n-butoxy, isobutoxy, sec-butoxy, tert-butoxy, cyclobutoxy, pentoxy, isopentoxy, neo-pentoxy, cyclopentoxy, hexoxy, and cyclohexoxy.

As used herein, an "alkyl group" means a linear, branched, or cyclic saturated hydrocarbon. Preferably, an alkyl group has between one and six carbon atoms. An alkyl group also refers to substituted alkyl groups, which may include substituents such as alkanoyloxy groups, alkenyl groups, alky groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred substituents are alkoxy groups, amino groups such as dialkylamino groups, diarylamino groups, carboxylic acid-containing groups, haloalkyl groups, halogens, hydroxyl groups, nitrile groups, nitro groups, and sulfonic acid groups.

Examples of preferred alkyl groups include, but are not limited to, methyl, ethyl, propyl, isopropyl, cyclopropyl, n-butyl, isobutyl, sec-butyl, tert-butyl, cyclobutyl, pentyl, isopentyl, neo-pentyl, 1-ethylpropyl, cyclopentyl, hexyl, and cyclohexyl.

As used herein, an "aryl group" means a phenyl group or naphthyl group, which is optionally substituted. Examples of substituents on aryl groups include, but are not limited to, alkanoyloxy groups, alkenyl groups, alkoxy groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred substituents are alkoxy groups, alkyl groups, amino groups such as dialkylamino groups and diarylamino groups, carboxylic acid-containing groups, haloalkyl groups, halogens, hydroxyl groups, nitrile groups, nitro groups, and sulfonic acid groups.

As used herein, an "arylalkyl group" means an aryl group attached to an alkyl group. An example of an arylalkyl group is a benzyl group.

Figure 3:
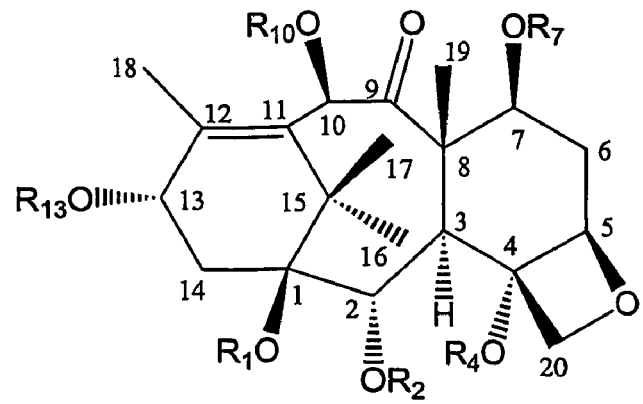
FIGS. 3 to 5 show non-limiting, exemplary compounds having a basic baccatin III structure.
Figure 4:
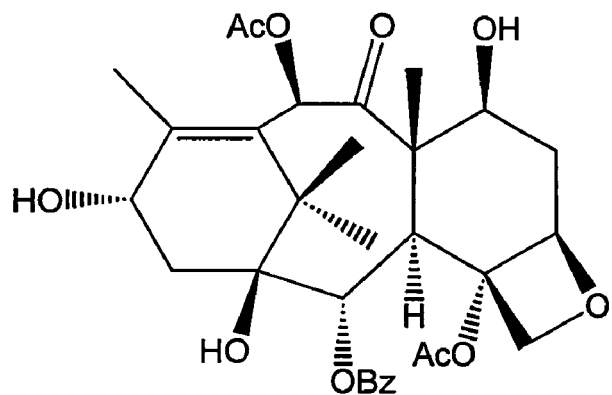
Figure 5:
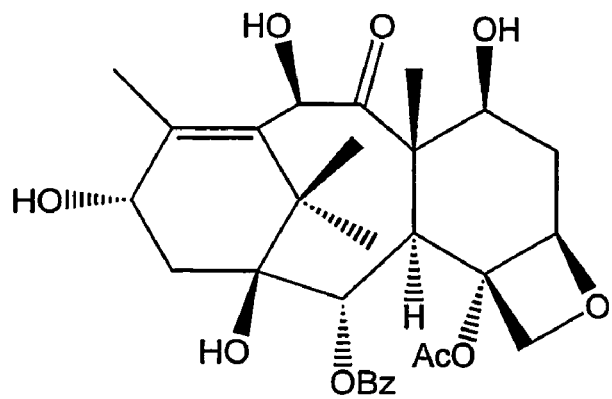
Figure 10:
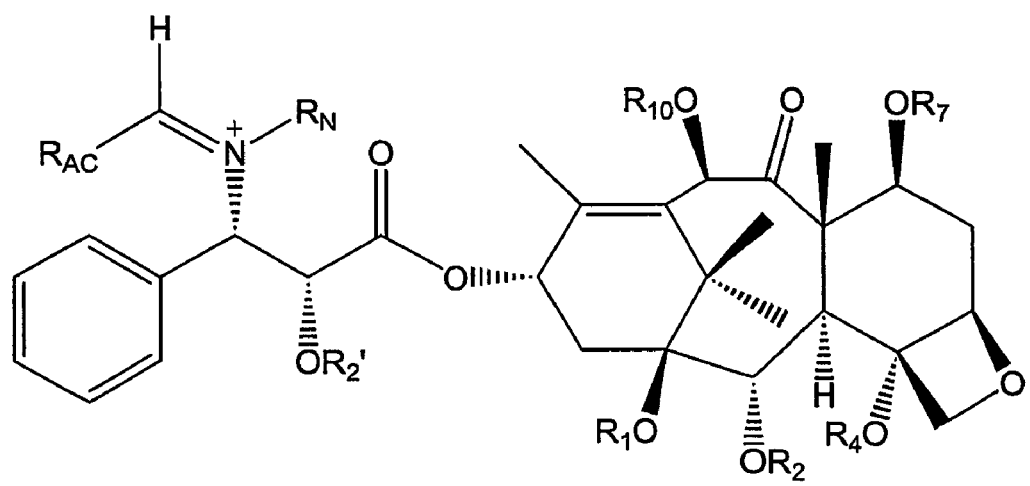

As used herein, a "basic baccatin III structure" means a compound having the formula as shown in FIG. 3, where each of $R_1$, $R_2$, $R_4$, $R_7$, $R_{10}$ and $R_{13}$ independently is hydrogen, an alkyl group, an acyl group, an aryl group, an arylalkyl group, a vinyl group, an ether group, an ester group, a glycoside group, an oxo group, or a hydroxyl protecting group. Included within the definition of a basic baccatin III structure is baccatin III, which has the formula as shown in FIG. 4, and 10-deacetylbaccatin III, which has the formula as shown in FIG. 5, where Ac is an acetyl or acetate group ($CH_3C(O)$—), and Bz is a benzoyl group ($PhC(O)$— or $C_6H_5C(O)$—).

As used herein, an "ester group" means a linear, branched, or cyclic substituent having an ester functionality, i.e., —C(O)O—. Examples of ester groups include acyl groups such as actyl and benzoy, which are bound to a hydroxyl group.

As used herein, an "ether group" means a linear, branched, or cyclic substituent having an ether functionality, i.e., —COC—. An examples of an ether group includes, but is not limited to, $HOCH_2CH_2OC(CH_2OH)H$—.

As used herein, a "glycoside group" or a "glycosyl group" means any of a number of sugar derivatives that contain a non-sugar group bonded to an oxygen or nitrogen atom and that on hydrolysis yield a sugar such as glucose. An example of a preferred gylcosyl group is xylosyl.

As used herein, a "halogen" means fluorine, chlorine, bromine, and/or iodine.

As used herein, a "heterocyclic group" is a saturated, unsaturated, or aromatic cyclic compound that contains at least one atom other than carbon, e.g., oxygen, nitrogen, or sulfur, in a ring. Examples of heterocyclic groups include furyls such as 2-furan, morpholino, piperadino, piperazino, N-methylpiperazino, pyrrollyl, pyridyl, and thiophene.

As used herein, a "hydroxyl protecting group" means a substituent of a hydroxyl group that is employed to block or protect the hydroxyl functionality, often while reacting other functional groups on the molecule, but not always. Examples of hydroxyl protecting groups are well known in the art and are described in J. W. Barton, "Protecting Groups in Organic Chemistry",: J. G. W. McOmie, ed., Plenum Press, New York, N.Y., 1973, and in T. W. Green and P. G. M. Wuts, "Protective Groups in Organic Synthesis", John Wiley & Sons, New York, N.Y., 1999. Each of these references is incorporated herein by reference in their entirety.

As used herein, an "oxo-group" means a substituent derived from the oxidation of a glycoside group such as a xyloside as described in U.S. Pat. No. 5,356,928.

Figure 16:
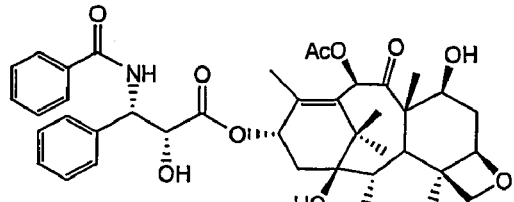
FIG. 16 shows a non-limiting taxane molecules produced by the present invention.
Figure 16:
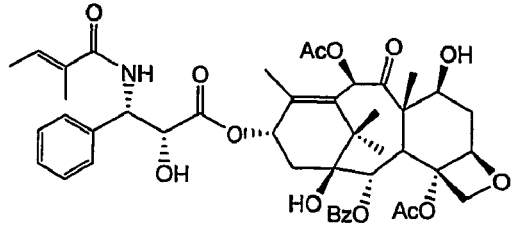
Figure 16:
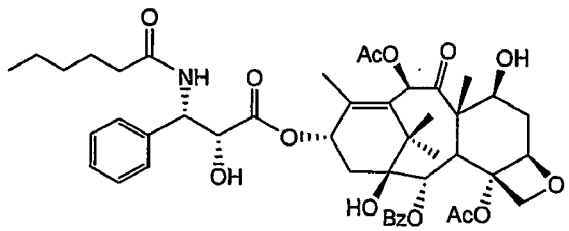
Figure 16:
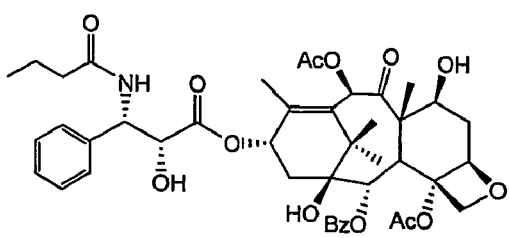
Figure 16:
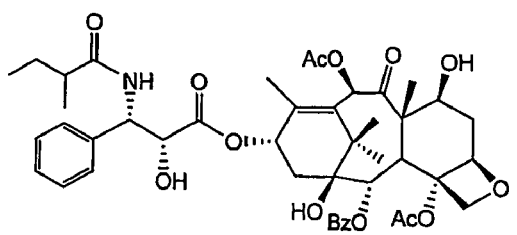
Figure 16:
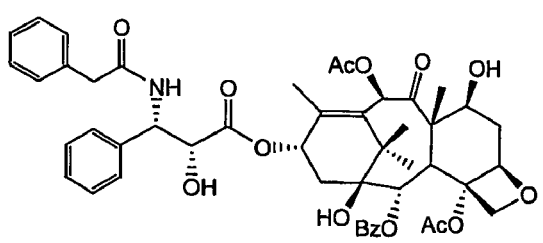
Figure 16:
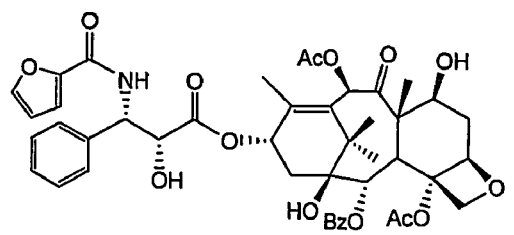
Figure 16:
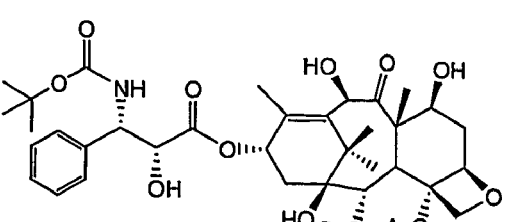
Figure 17:
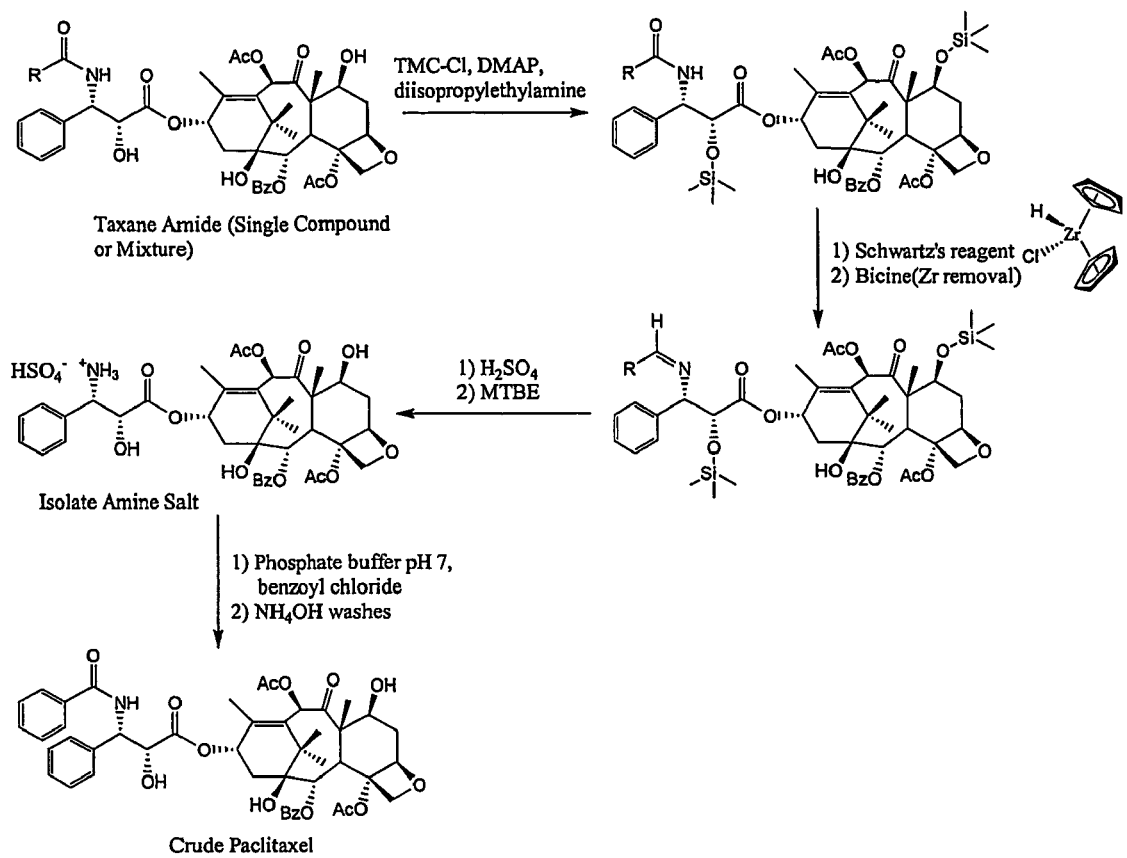
FIG. 17 shows a non-limiting, alternative embodiment of the present invention.

As used herein, "taxane or taxane molecule" means a molecule that contains a basic baccatin m structure with a (2R, 3S)—$C_6H_5CH(Rx)CH(OH)C(O)$— group forming an ester with the hydroxyl group located at the C-13 position of the basic baccatin III structure. The group represented by Rx can be an amino group, a salt of an amino group (e.g., an ammonium salt), an amino group which is protected with an amino protecting group, or a substituent which may be converted into an amino group. Various isomers, homologues, and analogues of the basic baccatin m structure, and of the (2R,3S)—$C_6H_5CH(Rx)CH(OH)C(O)$— group also are included in the definition of a taxane molecule. For example, a 10-deacetylbaccatin III structure is contemplated within the scope of a taxane molecule. Included within the definition of a taxane or taxane molecule are taxol A (paclitaxel), taxol B (cephalomanninc), taxol C, taxol D, taxol E, taxol F, taxol G, docetaxel (TAXOTERE®), (see, e.g., FIG. 16).

As used herein, a "vinyl group" means a linear or branched substituent having a carbon-carbon double bond. Examples of vinyl groups include, but are not limited to, 1-methyl-1-propenyl ($CH_3CH=C(CH_3)$—), and 2-methyl-1-propenyl (($CH_3)_2C=CH$—).

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of the recited processing steps. Further, it should be understood that the order of steps or order for performing certain actions are immaterial so long as the invention remains operable. Moreover, two or more steps or actions may be conducted simultaneously.

1. Starting Materials

Suitable starting materials for use in the present invention include, but not limited to, any taxane molecule with a C13 side chain containing an amide group. Taxanes containing an N-acylated phenylisoserine side chain at the C13 position may serve as a starting material for this invention. In addition the starting material may be a mixture of two or more of these taxanes. These compounds may have varying substitution patterns; for instance, the C10 position may contain an acetate or a hydroxyl, and the C7 position may contain a hydroxyl or a xylosyl group. Examples of these compounds may be found in FIG. 16 and more examples may be found in J. Natural Products, 1999, 62, 1448-1472, and Phytochemistry, 1999, 50, 1267-1304. Each publication is incorporated herein by reference in its entirety. It should be understood that potential starting materials are not limited to those found in these references. The starting materials may or may not be purified or isolated before reductively deoxygenating the taxane molecule.

Figure 2:
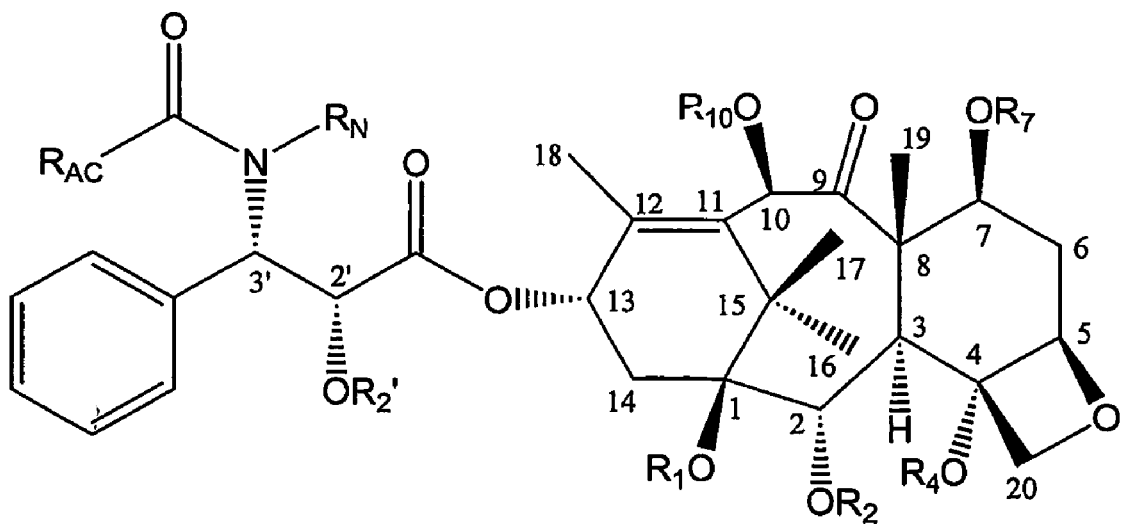
FIG. 2 shows a non-limiting, exemplary taxane produced by the present invention.

In a particular embodiment, the invention provides a method for converting a taxane molecule having the formula as shown in FIG. 1, where $R_1$ is hydrogen; $R_2$ is hydrogen, an acyl group or a hydroxyl protecting group; $R_4$ is an acetate group; $R_7$ is hydrogen, an alkyl group, an aryl group, an ester group, an ether group, a glycoside group, an oxo-group, or a hydroxyl protecting group; $R_{10}$ is hydrogen, an alkyl group, an aryl group, an ester group, an ether group, or a hydroxyl protecting group; $R_{2'}$ is a hydrogen, a hydroxyl-protecting group, an alkyl group, and aryl group, an ester, an ether group, or a vinyl group; $R_N$ is a hydrogen or an alkyl group; $R_{AC}$ is an alkoxy group, an alkyl group, an aryl group, an arylalkyl group, an ether group, a heterocyclic group, an acyl group, or a vinyl group; to another taxane molecule having the formula shown in FIG. 2, where $R_1$, $R_2$, $R_4$, $R_7$, $R_{10}$, $R_{2'}$, $R_N$, and $R_{AC}$ are as defined above. Other examples of $R_{AC}$ groups include, among others, acetyl ($CH_3C(O)$—), $HOC(O)$—, $CH_3OC(O)$—, $CH_3CH(OH)C(OH)(CH_3)$—, and $PhNHC(O)$—.

Figure 6:
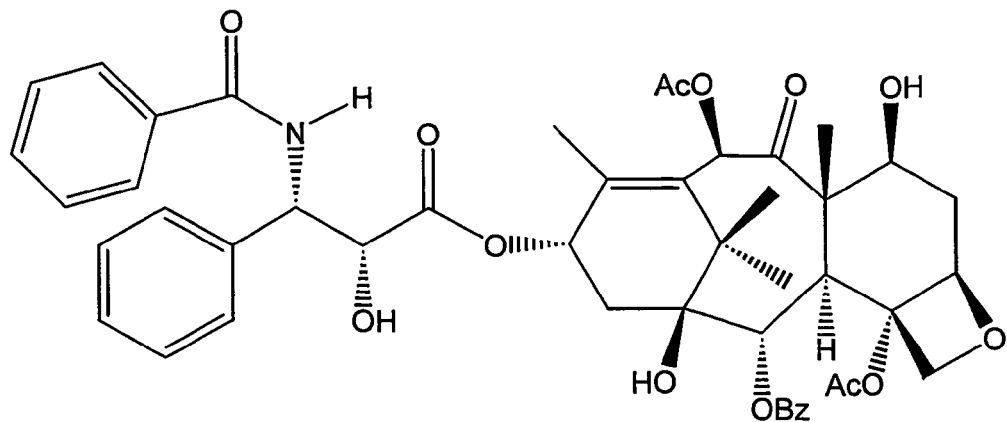
FIGS. 6 to 8 show non-limiting, exemplary taxanes for use in the present invention.
Figure 7:
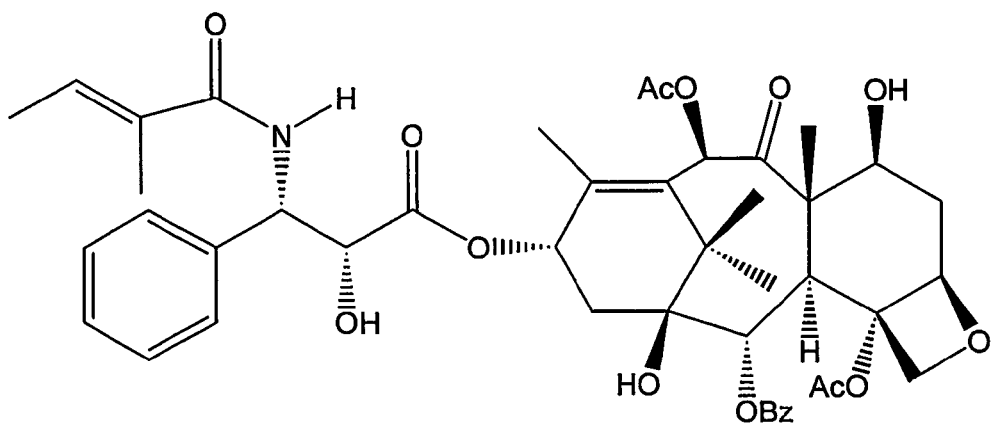
Figure 8:
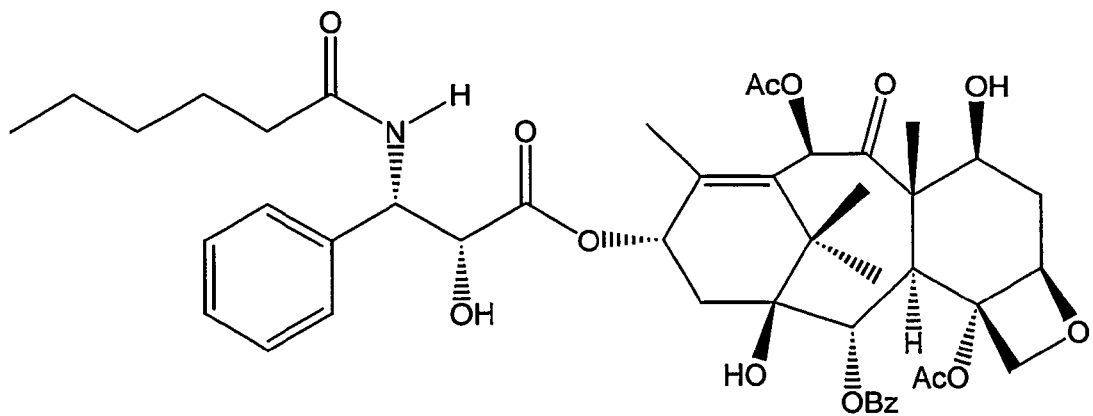

A more preferred starting material of the interconversion reaction of the invention is a taxane molecule having the formula as shown in FIG. 6. Another preferred starting material of the interconversion reaction of the invention is a taxane molecule having the formula, shown in FIG. 7. Another preferred structure material of the interconversion reaction of the invention is a taxane molecule having the formula shown in FIG. 8.

2. Protection of the Taxanes

The starting taxanes used in the present invention may or may not need to be OH— protected. In some cases OH protection may be desired and may be carried out such that one or more of the active groups, including but not limited to OH groups at C7, C10, and C2'; are protected with a hydroxyl protecting group. It has been shown that protection at the C2' hydroxyl group is especially important because this dramatically reduces the amount of side chain cleavage observed in the subsequent reductive deoxygenation step.

Figure 12:
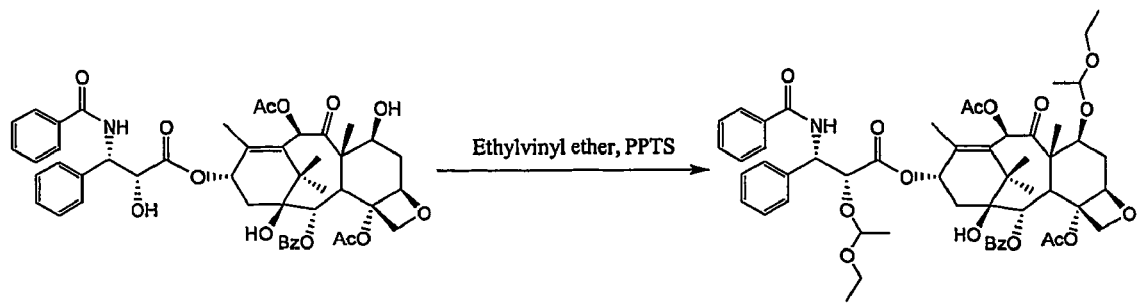
FIG. 12 shows a non-limiting alternative embodiment for protecting at least one hydroxyl group of a taxane amide molecule.
Figure 12:
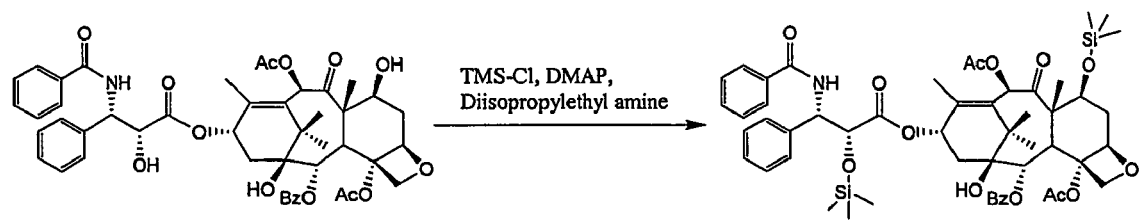

It should be understood that a hydroxyl-protecting group may remain on an end product. Examples of preferred hydroxyl protecting groups include acetate (Ac), benzoyl (Bz), trimethylsilyl (TMS), triethylsilyl (TES), 2,2,2-trichloroethoxycarbonyl (Troc), and ethoxylethyl ether (EE). Procedures for preparing the protected taxanes differ depending on the choice of protecting groups. In one preferred embodiment, the C2' and C7 hydroxyl groups are protected by treating the starting taxane in anhydrous THF with a hindered base such as diisopropylethylamine, followed by a catalytic amount of N, N-dimethylaminopyridine (DMAP), and then chlorotrimethylsilane from 0-25° C. In another embodiment, the starting taxane in anhydrous THF is treated with ethylvinyl ether and a catalytic amount of pyridinium para-toluenesulfonate. In both cases, typically a slight excess of protecting reagent is used per hydroxyl group being protected. A non-limiting example of preparing a protected taxanes amide is shown in FIG. 12.

3. Reductively Deoxygenating the Taxane Molecule

Figure 9:
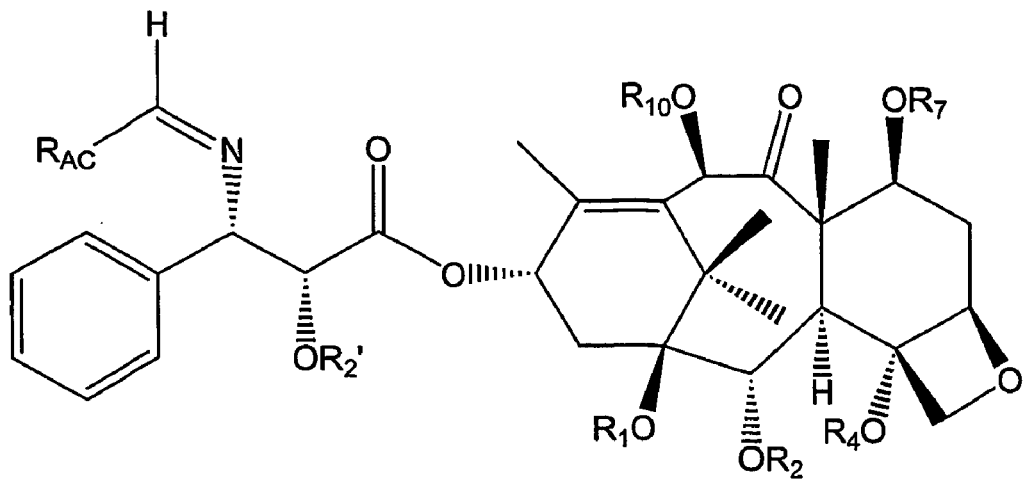
FIGS. 9-10 show non-limiting, exemplary taxane imines and iminum compounds of the present invention.

In the present invention, the hydroxyl protected or unprotected taxane amide may be reductively deoxygenated to produce a protected or unprotected taxane imine or iminium compound. If, in the starting taxane amide, $R_N$ is hydrogen, then a taxane imine may be formed. In one alternative embodiment, the imine compound generally has the formula shown in FIG. 9 where $R_1$, $R_2$, $R_4$, $R_7$, $R_{10}$, $R_{2'}$, and $R_{AC}$ are as earlier defined. If, in the starting taxane amide, $R_N$ is an alkyl group, then a taxane iminium compound may be formed. In one alternative embodiment, the iminium compound generally has the formula shown in FIG. 10 where $R_1$, $R_2$, $R_4$, $R_7$, $R_{10}$, $R_{2'}$, and $R_{AC}$ are as earlier defined.

Figure 13:
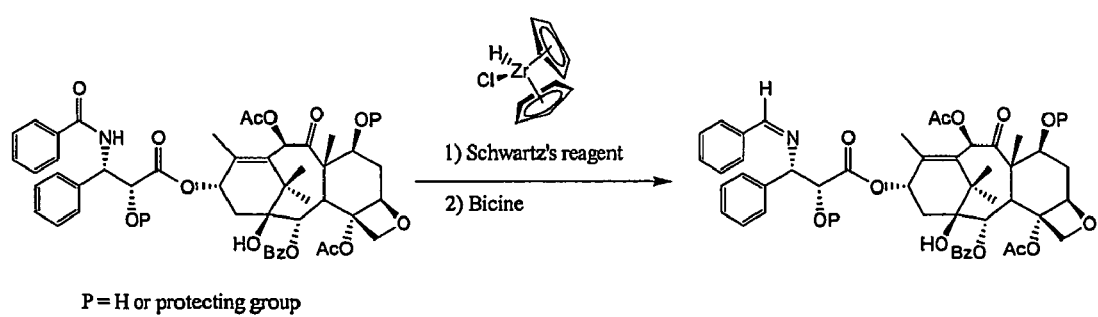
FIG. 13 shows an alternative embodiment of reducing a protected taxane amide with zirconocene chloride hydride (Schwartz's reagent).
Figure 14:
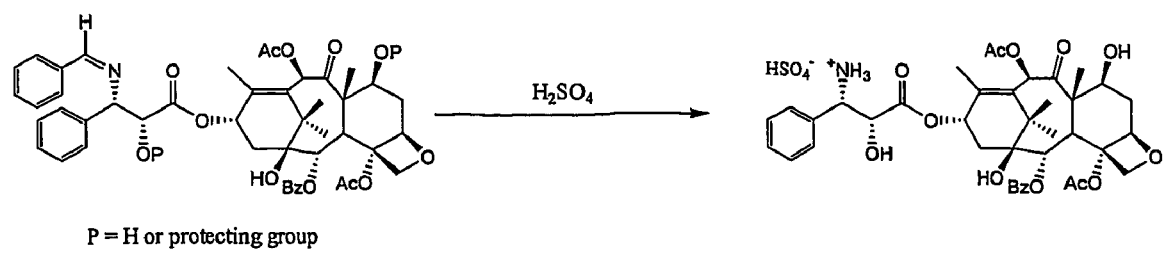
FIG. 14 shows an alternative embodiment of hydrolyzing a protecting taxane amide.

Throughout this invention the use of taxane imine compound includes, but is not limited to, taxane imines and taxane iminium compounds, including those described above. In one alternative embodiment, this reaction may be achieved by contacting the taxane amide with a suitable reducing agent, including but not limited to, a transition metal containing compound. The reductive deoxygenation may be effected using reagents known in the art. For example, the reductive deoxygenation step is preferably carried out using a zirconium hydride compound such as zirconocene chloride hydride (bis(cyclopentadienyl) zirconium chloride hydride), also known as Schwartz's reagent. A non-limiting example of this reaction is shown in FIG. 13. Contacting the taxane amide mixture with a reducing agent (e.g. transition metal reducing agent) provides a mixture comprising taxane imines.

Figure 18:
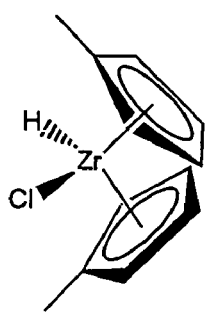
FIG. 18 shows a non-limiting examples of Schwartz's analogues for use in the present invention.
Figure 18:
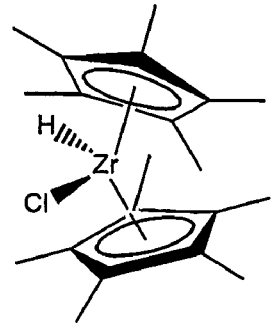
Figure 18:
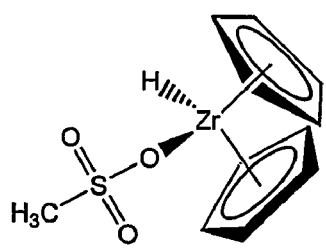
Figure 18:
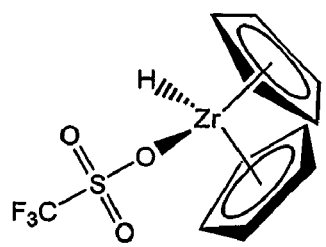
Figure 18:
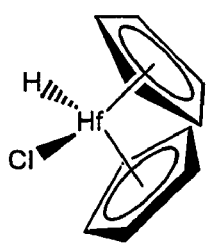
Figure 18:
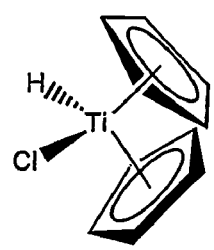

Other transition metal containing compounds or transition metal reducing agents, include, but are not limited to, titanium-containing reducing agents, hafnium-containing reducing agents, niobium-containing reducing agents, and molybdenum-containing reducing agents. Analogues and derivatives of Schwartz's reagent may also be used non-limiting examples of these reagents are shown in FIG. 18.

In one alternative embodiment, the amount of Schwartz's reagent used can vary from about 0.1 molar equivalent up to about 10 molar equivalents per mole of starting material. Preferably, about 3 or more molar equivalents of Schwartz's reagent are used. More specifically, the reductive deoxygenation reaction may consume 2 molar equivalents of Schwartz's reagent and an additional equivalent may be added to help drive the reaction to completion. Also, an additional equivalent of Schwartz's reagent may be needed if any hydroxyl groups are left unprotected as free hydroxyl groups will react and neutralize one equivalent of Schwartz's reagent. In one alternative embodiment, the Schwartz's reagent may be added to the taxane amide solution either as a dry powder or as a slurry in an appropriate solvent. Preferably, the solvent is anhydrous. Tetrahydrofuran is a preferred solvent. In one preferred embodiment, the taxane amide solution in anhydrous THF, and is added to a slurry of Schwartz's reagent also in anhydrous THF.

The reductive deoxygenation preferably is carried out in an inert environment, e.g., under a nitrogen or argon atmosphere. In a preferred embodiment, the Schwartz's reagent slurry and the taxane amide solution is cooled below ambient temperature prior to mixing. The pre-reaction slurry/solution temperature is preferably less than about 15° C., and more preferably less than about 10° C.

After addition of the taxane amide solution to the Schwartz's reagent slurry, hydrogen gas may be generated and the reaction solution will warm slightly as the reaction is mildly exothermic. Following complete addition, agitation of the reaction solution continues at a reduced temperature until the reaction is deemed complete. The reaction time is usually about 1-4 hours, but it may be longer. The reaction is deemed complete when the starting materials are substantially converted to a taxane imine. Preferably, the reaction is stopped when less than 10% of the starting material remains based on HPLC area of the starting taxane amide and the taxane imine.

4. Transition Metal Removal

Subsequent to completion of the reductive deoxygenation reaction, most of the transition metal and or transition metal by-products may be removed before proceeding with the next reaction. For example, in one alternative embodiment, all or substantially all of the transition metal or metal by-products may be removed such that the resultant mixture comprises less than 10,000 parts/million, preferably less than 5,000 parts/million, or more preferably less than 1000 parts per million of transition metal or transition metal by-products. For the present invention, removal of the transition metal or any metal by-products is optional.

It is understood that the removal of transition metal or any transition metal by-products may be performed separately or in conjunction with any other step described herein. Also, such removal step may be performed at various times during the process of the present invention.

Techniques for removing transition metal compounds or transition metal by-products are known in the art, including, but not limited to, complexation, precipitation, filtration, chelation, centrifugation, electrochemical methodology, chromatography, or any combination thereof. In one alternative embodiment, a chelating agent comprising a chelating agent effective to chelate a transition metal may be used to remove the transition metal compound or transition metal by-product. Such chelating agents may include, but are not limited to, ethylene diamine tetra acetic acid (EDTA), ethylene glycol (bis) aminoethyl ether tetra acetic acid (EGTA), 1,2-bis-(o-aminophenoxy)ethane, N, N, N', N'-tetra-acetic acid (BAPTA), N, N, N', N'-tetrakis-(2-pyridylmethyl)ethylenediamine (TPEN), nitrilotriacetic acid, TIRON®, and analogues and derivatives thereof.

In one alternative embodiment, the cooled reductive deoxygenation reaction solution is added to an excess of N,N-bis(2-hydroxyethyl)glycine (bicine) as an aqueous solution while maintaining the solution at an ambient temperature. About 2 or more equivalents of bicine preferably may be used based on the amount of transition metal present. Subsequently, the reaction may be worked-up, which may include additional treatment of the original reductive deoxygenation reaction solution with additional aqueous bicine solution. In a preferred embodiment, the aqueous bicine layer may be back extracted with an organic solvent, preferably THF or ethyl acetate, to recover any taxane imine in the bicine layer. A non-limiting example of this reaction is shown in FIG. 13.

5. Imine Hydroylsis

Figure 11:
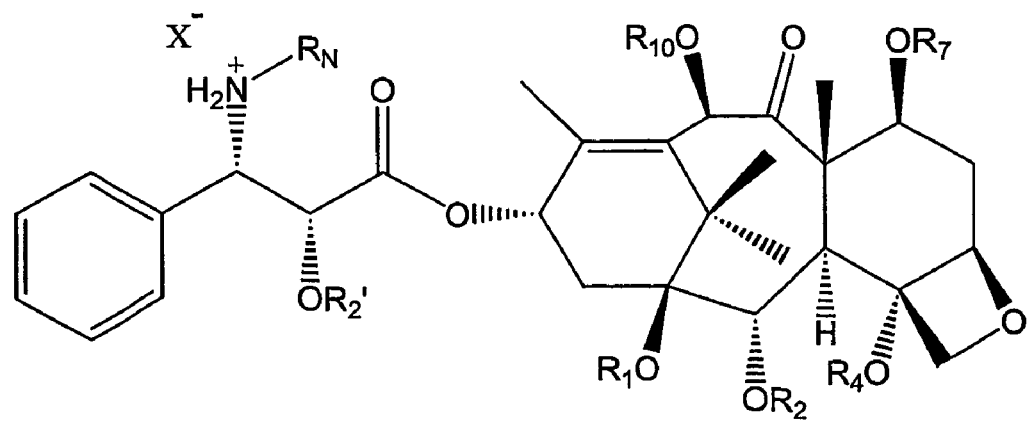
FIG. 11 shows a non-limiting, exemplary taxane amine salt of the present invention.

Following conversion to an imine compound, hydrolysis of the imine functionality produces an amine or amine salt at the C-3' position. Any common acid may be used to effect the hydrolysis of the imine compound. Such acids may include, but are not limited to: (i) hydrofluoric acid, hydrochloric, hydrobromic acid, or hydroiodic acid; (ii) nitric acid and or other nitrogen containing acids; (iii) sulfuric acid or other sulfur containing acids; (iv) carboxcylic acids, except for trifluro acetic acid; (v) phosphoric acid or other phosphate containing acids; (vi) tartaric acid; (vii) perchloric acid; (viii) p-tolulene sulfuric acid; (ix) picric acid. Preferably, the acid is sulfuric acid. The acid may be aqueous and/or in solution with a protic solvent, e.g. ethanol and/or methanol. In one alternative embodiment of the present invention, the amine salt may have the formula shown in FIG. 11, where $R_1$, $R_2$, $R_4$, $R_7$, $R_{10}$, $R_2'$, and RN are as defined above. Here, X may include a deprotonated inorganic acid comprising a halogen. Such acids may include, but are not limited to, hydrofluoric acid, hydrochloric, hydrobromic acid, or hydroiodic acid. Also, X may include: (i) deprotonated nitric acid and or other nitrogen containing acids; (ii) deprotonated sulfuric acid or other sulfur containing acids; (iii) deprotonated carboxcylic acid, except for trifluro acetic acid; (iv) deprotonated phosphoric acid or other phosphate containing acids; (v) deprotonated tartaric acid; (vi) deprotonated perchloric acid; (vii) deprotonated p-Tolulene sulfuric acid; (viii) deprotonated picric acid. In an alternative embodiment, about 2 or more molar equivalents of acid should be used per mole of imine.

Hydrolysis of the imine compound may be carried out at or about ambient temperature. Also, hydrolysis may be carried out on an isolated or purified taxane imine. Preferably, an aqueous solution of acid is added directly to the reductive deoxygenation reaction solution after zirconium removal. The amine hydrolysis step may be employed before or after the addition of the anti-solvent (see below) to produce the taxane amine from the reaction mixture.

Figure 19A:
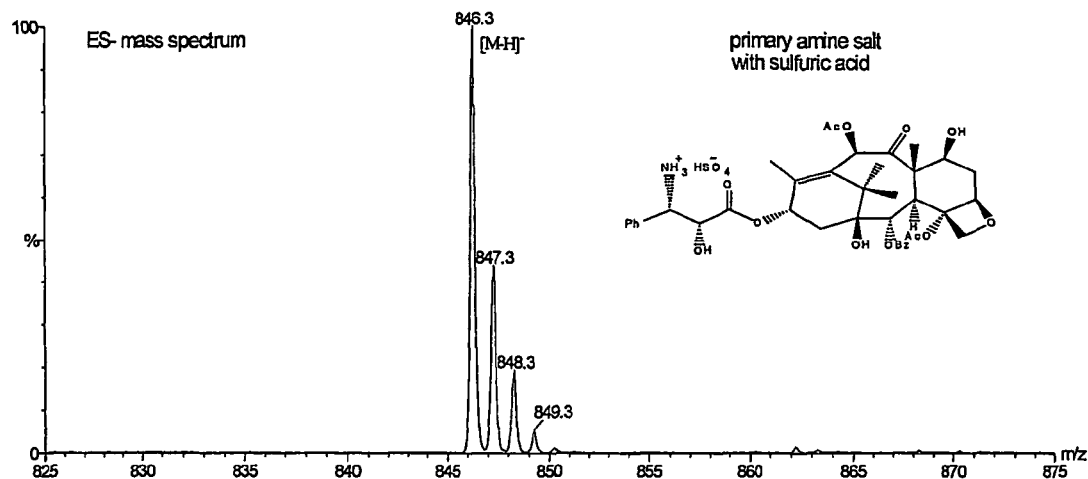
FIG. 19A shows an electrospray ionization mass spectrum of a primary amine salt with sulfuric acid.
Figure 19B:
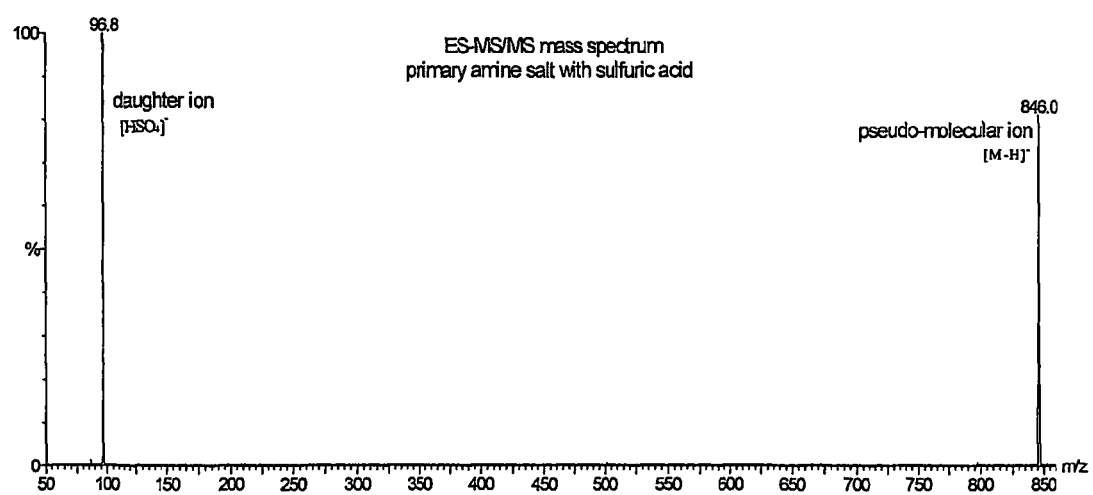
FIG. 19B shows an ES-MS/MS mass spectrum of a primary amine salt with sulfuric acid.

In one embodiment, the presence of the amine salt was confirmed using ES-MS/MS mass spectroscopy (Micromass Quattro LC Mass Spectrometer) and electrospray ionization mass spectrum. FIG. 19A shows an eletrospray ionization mass spectrum of a primary amine salt with sulfuric acid. This amine salt was produced by the amine hydrolysis step, and then isolated in the solidification step described herein. The spectrum shows the correct mass and anticipatedisotope peak distribution profile of the amine salt, having a mw 847. FIG. 19B shows an ES-MS/MS mass spectrum of a primary amine salt with sulfuric acid. The amine salt was produced during the amine hydrolysis step and then isolated in the solidification step described herein. The spectrum shows a daughter ion spectrum of the pseudo-molecular ion, [M—H]— of m/z 846. Here, the spectrum shows a single intense daughter ion [$HSO_4$]— at m/z 96.8.

In addition to hydrolyzing the taxane imine, the acid can also serve to remove the hydroxyl protecting groups if the protecting groups used are sensitive to acid. Examples of acid sensitive protecting groups include, but are not limited to, trimethylsilyl, triethylsilyl, and ethoxyethyl ether. Therefore, care should be taken in the selection of an appropriate hydrolysis reagent to avoid unwanted removal of protecting groups that may be present on the taxane molecule. However, it may be desirable to remove certain protecting groups on a taxane molecule to facilitate conversion of a "protected" taxane molecule to a known taxol derivative, e.g., removal of a silyl or ether protecting group from the C7, C10, and/or C2' hydroxyl groups. Accordingly, if an acid is to perform additional functions in the reaction, the amount of acid used in the reaction should be appropriately adjusted.

6. Solidification of Taxane Amine Salt

The taxane amine salt may be solidified by adding an appropriate amount of a less polar solvent, preferably methyl tert-butyl ether. Other solvents, such as dichloromethane, heptane, hexane, toluene, or trifluorotoluene may also be used. Once solidified, the taxane amine salt can be easily filtered thus providing purification. Essentially all non-amine by-products or unreacted starting material remain in the filtrate and are thus removed.

7. Conversion of the Taxane Amine Salt to Paclitaxel

Figure 15:
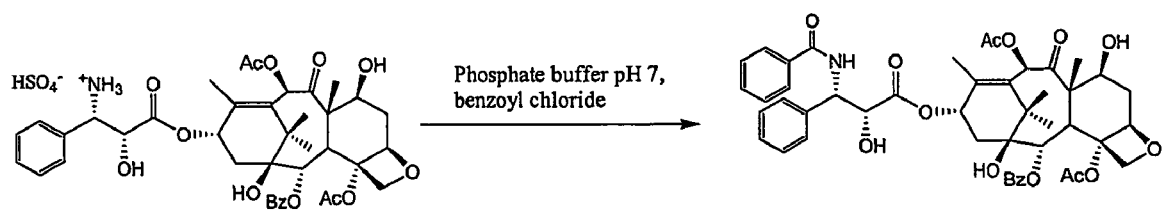
FIG. 15 shows an alternative embodiment of benzolylating a taxane amine.

The taxane amine salt may be converted into paclitaxel or other useful taxanes by reacting the amine in various ways. For instance, the appropriate amine salt may be converted into paclitaxel by reacting it with benzoyl chloride or some other benzoylating agent. This may be accomplished by first dissolving the amine salt in a solvent, preferably THF and then neutralizing the amine salt with excess base, preferably an inorganic base, most preferably sodium carbonate, followed by addition of a slight excess of a benzoylating agent, preferably benzoyl chloride. A non-limiting example of such a reaction is shown in FIG. 15. Other taxane amides may be produced by varying the acylating agent.

It has been shown however, that when the benzoylating step procedure is followed the production of a specific impurity has been found. The structure of this impurity has not been conclusively established but was found to have a molecular weight of 1104 Daltons. This impurity has also been found to be difficult to remove in downstream purification steps. The formation of this impurity was found to be dependent on the pH of the benzoylation step; therefore the moderation of base used to neutralize the amine salt was important. In a preferred alternative embodiment, the amine salt is dissolved in THF and then treated with benzoyl chloride followed by phosphate buffer of about pH 7 such that the final pH of the benzoylation solution was about 4 to 6. Using the phosphate buffer in place of the excess base dramatically reduced the formation of this impurity.

Once the benzoylation step is deemed complete (<2% amine remaining by HPLC area) the crude paclitaxel may be worked up by separating and removing the aqueous phosphate layer, washing the organic layer with saturated NaCl solution, drying the organic layer with a drying agent, preferably magnesium sulfate ($MgSO_4$), and precipitating the dried organic layer into 4-6X hexane or heptane. The product precipitate can then be easily filtered and dried and is adequate for further purification. Following this procedure it was found that after drying, the formation of two impurities was observed. Both of these impurities had molecular weights of 871 Daltons and were determined to be oxetane ring-opened paclitaxel derivatives. These derivatives are well known in the literature and are known to form in the presence of eletrophilic reagents such as acid chlorides. Therefore, residual amounts of benzoyl chlorides were determined to be the cause of these impurities.

In a preferred alternative embodiment, about 0.5 molar equivalents of amines, preferably primary amines, most preferably ammonium hydroxide was added to the benzoylation reaction solution after the reaction was deemed complete to react with any residual benzoyl chloride. The aqueous layer is then separated and removed and the organic layer is washed twice more with the appropriate amine followed by a saturated NaCl solution wash each time. The organic layer is then dried with a drying agent, preferably magnesium sulfate ($MgSO_4$), and precipitating the dried organic layer into 4-6X hexane or heptane. Following this protocol, the formation of the MW 871 impurities was dramatically reduced.

The end product and/or isolated intermediates may be analyzed using analytical techniques known in the art such as infrared (IR) spectroscopy, nuclear magnetic resonance (NMR) spectroscopy, e.g., $^1$H-NMR and $^{13}$C-NMR, high performance liquid chromatography (HPLC), e.g., reversed phase HPLC, and/or mass spectrometry (MS), e.g., electrospray ionization MS (ES MS) and matrix-assisted laser adsorption ionization MS (MALDI-MS). Combinations of these techniques also may be used, e.g., HPLC-MS.

In an embodiment of the above-described methodology, the invention is directed to methods of interconverting mixtures of taxane molecules, e.g., from biomass or biomass extracts, to a particular taxane molecule, e.g., paclitaxel. The methodology for interconversion of mixtures of taxane molecules into a specific taxane molecule generally is the same as for the interconversion of a single taxane molecule into another single taxane molecule.

VI. EXAMPLES

Example 1

The following materials may be used in the present invention as described below:
HPLC (XTerra Column; Water-acetonitrile gradient with 0.05% formic acid); UV detection
Taxane amides (500 g);
3 Liters dry THF;
7.2 g 4-Dimethylamino)pyridine (DMAP) [1122-58-3];
338 mL (Hünig's Base) [7175-49-7] N-ethyldiisopropyl amine;
165 mL Chlorotrimethylsilane (TMSC1) [75-774];
469 g Bis(cyclopentadienyl)zirconium chloride hydride (Schwartz's Reagent);
Bicine solution (1M) [150-25-4];
1 Liter Ethyl acetate;
350 mL 10% sulfuric acid solution;
10 Liters Methyl tert-butyl ether (MTBE);
4 Liters 4:1 MTBE:THF;
317 g Sodium bicarbonate;
68 mL Benzoyl chloride [Free of benzene ring substituted impurities];
15 Liters heptane; and
3 Liters Brine solution.

STEP 1: To a solution of taxane amides (500 g, 586 mmol) in 1.5 L dry THF under nitrogen, 7.2 g DMAP (590 mmol) is added, followed by 338 mL N-ethyl diisopropyl amine (Hünig's Base; 1.47 mol) and slow addition of TMS chloride (1.47 mol) over about an hour. The reaction is stirred for another hour at RT. HPLC (XTerra RP C-18 Column; Water-acetonitrile gradient with 0.05% formic acid) should show no taxanes at this time. The reaction is cooled to 0° and then filtered. The salt is washed with 500 mL dry THF.

STEP 2: The solution from STEP 1 is cooled to 0° under nitrogen and added slowly to a slurry of 469 g (1.97 mol) Bis(cyclopentadienyl)zirconium chloride hydride (Schwartz's Reagent) in 1 L dry THF under nitrogen. There is hydrogen evolution at this point. Thus, the reaction vessel should be large enough to accommodate some foaming. The reaction is stirred at 0° for about 4 hours while monitoring by HPLC, and is then taken to ca. 90% completion, and quenched before significant side-products form.

STEP 3: The reaction is quenched with aqueous bicine solution (1 M; 2.8 L); the layers are separated and the organic phase is washed with a second 2.8 L of bicine solution. The combined aqueous layers are extracted once with 500 mL ethyl acetate, and the combined organic phase is treated with 350 ML 10% sulfuric acid solution with good stirring, for one hour.

STEP 4: The hydrolyzed mixture from STEP 3 is added to 10 L MTBE, stirred well for 30 minutes, and filtered. The solid amine salt is washed with 2×2 L 4:1 LMTBE:THF. The LMTBE and LMTBE:THF solutions are saved to recover unreacted taxanes. The solid is dissolved in 2 L THF, and then 200 mL water is added, followed by 317 g solid $NaHCO_3$. Caution: There is some foaming at this point. Preferably, the sodium bicarbonate is added slowly. The mixture is stirred well for 15 min after the addition of the sodium bicarbonate. Then, 68 mL Benzoyl chloride is added, and the reaction is stirred well for 1 hour. The reaction is then treated with 3 L brine, and the layers separated. The brine solution is washed once with 500 mL ethyl acetate. The combined organic layers are dried over $MgSO_4$ and filtered. The resulting paclitaxel solution is then added to 15 L heptane, and the precipitate is filtered and vacuum-dried overnight, providing a 75-80% yield (i.e., approximately 375-400 g). The paclitaxel is 70% to 90% pure, or 75% to 95% pure, or 80% to 90% pure, or 90% to 95% pure. If desired, the paclitaxel may be purified further.

Example 2

This example demonstrates the conversion of a taxane amide mixture composed mainly of taxol C and taxol E into taxol A (paclitaxel)

A taxane amide mixture composed of 2.6% taxol A, 4.8% taxol B, 54.1% taxol C, 0.2% taxol D, 32.0% taxol E, and 4.2% taxol F (100 g., ~117 mmol) was dissolved in 500 mL anhydrous THF. Then solid Schwartz's reagent (137 g., 533 mmol) was added at 5° C. and the reaction was stirred at that temperature under nitrogen and was monitored by HPLC. After 4 hours the reaction was stopped by stirring it with 800 mL 1M bicine solution for 30 minutes. The organic layer was stirred with another 800 mL 1M bicine for 30 minutes. The combined aqueous layers were stirred with 150 mL ethyl acetate for 20 minutes. The THF and ethyl acetate layers were combined and treated with 70 mL 10% $H_2SO_4$ for 1 hour followed by the slow addition of 1800 mL methyl tert-butyl ether (MTBE) and an additional 30 minutes of stirring. The taxane amine salt was filtered and washed with MTBE:THF 3:1 and then dissolved in 200 mL THF. Then 100 mL of water, 36 grams of $NaHCO_3$ (429 mmol), and 14 mL of benzoyl chloride (234 mmol) was added. The reaction was complete after 1 hour and was washed with 100 mL water, then 100 mL saturated NaCl solution, and finally dried with $MgSO_4$. The filtered solution was next precipitated in 1200 mL of heptane. After filtration and vacuum drying, the crude paclitaxel was obtained (51 grams, purity 76.5%, yield 44%).

Example 3

This example demonstrates the conversion of a taxane amide mixture composed mainly of taxol A and taxol B into taxol A (paclitaxel) using ethoxyethyl ether protection.

A taxane amide mixture composed of 51.4% taxol A, 28.2% taxol B, 7.6% taxol C, 0.5% taxol D, 1.7% taxol E, 3.3% taxol F, and 0.6% taxol G (481.6 g., ~578.8 mmol) was dissolved in 2.5 L anhydrous THF followed by the addition of 3.63 grams of pyridinium para-toluenesulfonate (14.5 mmol) and 138.4 mL ethylvinyl ether (1.45 mol). The reaction was stirred at room temperature and after 16 hours was complete. The reaction solution was next cooled down to 5° C. and 2.03 mL of triethylamine was added followed by 441.8 grams of solid Schwartz's reagent (1.72 mol). The reaction was stirred at 5° C. and monitored by HPLC. After 4 hours the reaction was stopped by stirring it with 2.58 L 1M bicine solution for 30 minutes. The organic layer was stirred with another 2.58 L 1 M bicine for 30 minutes. The combined aqueous layers were stirred with 500 mL ethyl acetate for 20 minutes. The THF and ethyl acetate layers were combined and treated with 336.7 mL 10% $H_2SO_4$ for 1 hour followed by the slow addition of 7.5 L methyl tert-butyl ether (MTBE) and an additional 1 hour of stirring. The taxane amine salt was filtered and dissolved in 1 L THF. Another 85 mL 10 $H_2SO_4$ was added and stirred for 30 minutes followed by the slow addition of 3 L MTBE followed by 30 minutes of stirring. The amine salt was filtered and washed with 3×1 L MTBE:THF 3:1. The amine salt was then dissolved in 1 L THF. Then 200 mL water followed by 212.7 grams $NaHCO_3$ (2.53 mol) was added cautiously. Next 80 mL benzoyl chloride (687 mmol) was added and the reaction was stirred at room temperature for 1 hour. The reaction solution was next washed with water, dried with $MgSO_4$, filtered, and precipitated into 6 L heptane. Filtration and vacuum drying yielded the crude paclitaxel (507 grams, purity 78.2%, yield 80%).

Example 4

This example demonstrates the conversion of a taxane amide mixture composed mainly of taxol C and taxol E into taxol A (paclitaxel) using ethoxyethyl ether protection.

A taxane amide mixture composed of 2.6% taxol A, 4.8% taxol B, 54.1% taxol C, 0.2% taxol D, 32.0% taxol E, and 4.2% taxol F (10 g., ~11.7 mmol) was dissolved in 50 mL anhydrous THF followed by the addition of 75 mg of pyridinium para-toluenesulfonate (0.3 mmol) and 2.8 mL ethylvinyl ether (29.7 mmol). The reaction was stirred at room temperature and after 16 hours was complete. The reaction solution was next cooled down to −5° C. and 13.7 grams of solid Schwartz's reagent (53.4 mmol). The reaction was stirred at 5° C. and monitored by HPLC. After 6 hours the reaction was stopped by stirring it with 80 mL 1M bicine solution for 30 minutes. The organic layer was stirred with another 80 mL 1M bicine for 30 minutes. The combined aqueous layers were stirred with 5 mL ethyl acetate for 20 minutes. The THF and ethyl acetate layers were combined and treated with 7 mL 10% $H_2SO_4$ for 1 hour followed by the slow addition of 150 mL methyl tert-butyl ether (MTBE) and an additional 1 hour of stirring. The taxane amine salt was filtered and dissolved in 20 mL THF. Another 5 mL 10% $H_2SO_4$ was added and stirred for 30 minutes followed by the slow addition of 60 mL MTBE followed by 30 minutes of stirring. The amine salt was filtered and washed with 3×5 mL MTBE:THF 3:1. The amine salt was then dissolved in 20 mL THF. Then 5.2 grams $NaHCO_3$ (61.9 mmol) was added cautiously. Next 1.4 mL benzoyl chloride (12 mmol) was added and the reaction was stirred at room temperature for 1 hour. The reaction solution was next washed with water, dried with $MgSO_4$, filtered, and precipitated into 120 mL heptane. Filtration and vacuum drying yielded the crude paclitaxel (5.81 grams, purity 76%, yield 43.6%).

Example 5

This example demonstrates the conversion of a taxane amide mixture composed mainly of taxol B into taxol A (paclitaxel) using trimethylsilyl ether protection.

A taxane amide mixture composed of 2.5% taxol A, 83.1% taxol B, 1.9% taxol C, 0.7% taxol D, 5.8% taxol E, 0.3% taxol F, 0.9% taxol G (10 g., ~12 mmol) was dissolved in 30 mL anhydrous THF followed by the addition of 72 mg of N, N-dimethylaminopyridine (DMAP) (0.59 mmol), 5.13 mL diisopropylethyl amine (DIPEA) (29.43 mmol), and 3.72 mL chlorotrimethylsilane (TMS-Cl) (29.31 mmol). The reaction was stirred at room temperature and after 1 hour was complete. The reaction mixture was then cooled to 0° C. and filtered (to remove amine hydrochloride salts). The filtrate was added to a slurry of 8.44 gram Schwartz's reagent (32.83 mmol) in 20 mL anhydrous THF at 0° C. under nitrogen. After 4 hours the reaction was stopped by stirring it with 50 mL 1M bicine solution for 30 minutes. The organic layer was stirred with another 50 mL 1M bicine for 30 minutes. The combined aqueous layers were stirred with 10 mL ethyl acetate for 20 minutes. The THF and ethyl acetate layers were combined and treated with 7 mL 10% $H_2SO_4$ for 1 hour followed by the slow addition of 210 mL methyl tert-butyl ether (MTBE) and an additional 30 minutes of stirring. The amine salt was filtered and dissolved in 30 mL THF and 2 mL water followed by 7.4 grams $NaHCO_3$ (88.1 mmol) was added cautiously. Then 1.36 mL benzoyl chloride (12 mmol) was added and the reaction was stirred at room temperature for 15 minutes. The reaction solution was then washed with 20 mL saturated NaCl solution, dried over $MgSO_4$, filtered, and precipitated into 120 mL heptane. Filtration and vacuum drying yielded the crude paclitaxel (9.28 grams, purity 87.8%, yield 86.6%).

Example 6

This example demonstrates the conversion of a taxane amide mixture composed mainly of taxol A into taxol A (paclitaxel) using trimethylsilyl ether protection.

A taxane amide mixture composed of 79.2% taxol A, 17.4% taxol B, 1.6% taxol C, and 0.3% taxol E (2.5 g., ~2.9 mmol) was dissolved in 7.5 mL anhydrous THF followed by the addition of 18 mg of N, N-dimethylaminopyridine (DMAP) (0.13 mmol), 1.54 mL diisopropylethyl amine (DIPEA) (8.8 mmol), and 1.1 mL chlorotrimethylsilane (TMS-Cl) (8.7 mmol). The reaction was stirred at 0° C. and after 1 hour was complete. The reaction mixture was then filtered (to remove amine hydrochloride salts). The filtrate was added to a slurry of 2.26 gram Schwartz's reagent (8.8 mmol) in 3.3 mL anhydrous THF at 5° C. under nitrogen. After 4 hours the reaction was stopped by stirring it with 13 mL 1M bicine solution for 30 minutes. The organic layer was stirred with another 13 mL 1M bicine for 30 minutes. The combined aqueous layers were stirred with 2.5 mL ethyl acetate for 20 minutes. The THF and ethyl acetate layers were combined and treated with 1.75 mL 10% $H_2SO_4$ for 1 hour followed by the slow addition of 65 mL methyl tert-butyl ether (MTBE) and an additional 30 minutes of stirring. The amine salt was filtered and dissolved in 10 mL THF and 0.41 mL benzoyl chloride (3.5 mmol), 2.5 mL saturated NaCl solution, and 12.5 mL pH 7 phosphate buffer was added and the reaction was stirred at room temperature for 15 minutes. The reaction solution was then treated with 0.17 mL concentrated ammonium hydroxide and stirred for 15 minutes. The solution was then washed with 5 mL saturated NaCl solution. The separated organic layer was dried over 1.25 grams $MgSO_4$, filtered, and precipitated into 73 mL heptane. Filtration and vacuum drying yielded the crude paclitaxel (2.3 grams, purity 80.9%, yield 76.5%).

Example 7

This example demonstrates the conversion of N-methyl taxol A into N-methyl taxol C.

A sample of N-methyl taxol A (3.5 grams, 4.0 mmol) was dissolved in 10 mL anhydrous THF followed by the addition of 30 mg of N, N-dimethylaminopyridine (DMAP) (0.24 mmol), 2.0 mL diisopropylethyl amine (DIPEA) (11.5 mmol), and 1.4 mL chlorotrimethylsilane (TMS-C1) (11.4 mmol). The reaction was stirred at 0° C. and after 1 hour was complete. The reaction mixture was then filtered (to remove amine hydrochloride salts). The filtrate was added to a slurry of 3.0 gram Schwartz's reagent (11.8 mmol) in 5 mL anhydrous THF at 0° C. under nitrogen. After 4 hours the reaction was stopped by stirring it with 18 mL 1M bicine solution for 30 minutes. The organic layer was stirred with another 18 mL 1M bicine for 30 minutes. The combined aqueous layers were stirred with 7 mL ethyl acetate for 20 minutes. The THF and ethyl acetate layers were combined and treated with 2.2 mL 10% $H_2SO_4$ for 1 hour followed by the slow addition of 83 mL methyl tert-butyl ether (MTBE) and an additional 30 minutes of stirring. The amine salt was filtered and dissolved in 12 mL THF and 0.6 mL hexanoyl chloride (4.0 mmol), 3.1 mL saturated NaCl solution, and 17 mL pH 7 phosphate buffer was added and the reaction was stirred at room temperature for 15 minutes. The reaction solution was then treated with 0.22 mL concentrated ammonium hydroxide and stirred for 15 minutes. The solution was then washed with 6 mL saturated NaCl solution. The separated organic layer was dried over 1.7 grams $MgSO_4$, filtered, and precipitated into 95 mL heptane. Filtration and vacuum drying yielded the crude paclitaxel (2.83 grams, yield 75%).

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

The content of each of the patent and non-patent documents referred to herein is expressly incorporated herein by reference in its entirety.

The invention may be embodied in other specific forms without departing form the spirit or essential characteristics thereof The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

Also, the invention may suitably comprise, consist of or consist essentially of the elements or process steps described herein. Further, the invention described herein suitably may be practiced in the absence of any element or process step which is or is not disclosed herein.

We claim:

1. A method for forming a taxane or precursor or analog thereof from a raw material, the raw material comprising a compound represented by the formula below:

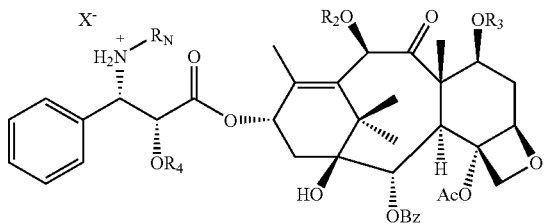

wherein, $R_2$ is H, Ac or a protecting group;

$R_3$ is H, xylosyl or protecting group;

$R_4$ is H or protecting group;

$R_N$ is H or an alkyl group; and

X=deprotonated sulfuric acid or deprotonated sulfur containing acid; deprotonated nitric acid or other nitrogen containing acid; deprotonated carboxylic acid, except trifluoro acetic acid; deprotonated phosphoric acid or any phosphorus containing acid; deprotonated tartaric acid; deprotonated p-toluene sulfonic acid; or deprotonated picric acid; and wherein said taxane or precursor or derivative thereof is in a solid, purified form;

the method comprising benzoylating the raw material with a benzoylation solution comprising a benzoylating agent and a buffer such that the pH of the benzoylation solution is about 4 to about 6.

2. The method of claim 1, wherein the buffer comprises a phosphate buffer.

3. The method of claim 2, wherein the phosphate buffer is of about pH 7.

4. The method of claim 1, wherein $R_2$ is Ac and $R_3$ is H.

5. The method of claim 1, wherein $R_2$ is H and $R_3$ is H.

6. The method of claim 1, wherein $R_2$ is Ac and $R_3$ is xylosyl.

7. The method of claim 1, wherein $R_2$ is H and $R_3$ is xylosyl.

8. The method of claim 1, wherein $R_2$, $R_3$ and $R_4$ is the protecting group selected from the group consisting of triethylsilyl, trimethylsilyl, trichloroethoxycarbonyl and ethoxyethyl ether.

9. The method of claim 1, wherein $R_3$ and $R_4$ is a protecting group selected from the group consisting of triethylsilyl, triethylsilyl, trichloroethoxycarbonyl and ethoxyethyl ether.

10. The method of claim 1, wherein $R_3$ and $R_4$ is trimethylsilyl.

11. The method of claim 1, wherein $R_4$ is a protecting group selected from the group consisting of triethylsilyl, triethylsilyl, trichloroethoxycarbonyl and ethoxyethyl ether.

12. The method of claim 1, wherein $R_4$ is trimethylsilyl.

13. A method of forming a taxane amine or salt comprising the steps of: (i) contacting a taxane imine according to the formula below with a protic solvent;

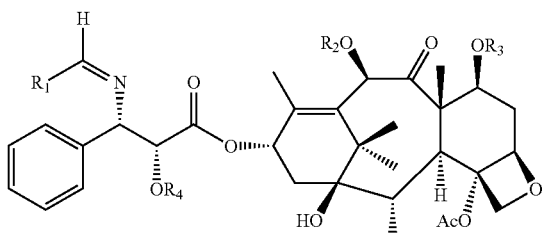

wherein, $R_1$=alkyl, aryl, carbonyl or ether group;
$R_2$=H, alkyl, aryl, ester, ether or protecting group;
$R_3$=H, alkyl, aryl, ether, ester, xylosyl, or protecting group;
$R_4$=H or protecting group;
(ii) contacting the taxane imine with an acid useful to effect hydrolysis of the imine; and
(iii) isolating a solid, purified taxane amine or salt by adding a solvent that is less polar than said protic solvent.

14. The method of claim 1, wherein X is a deprotonated nitric acid or other nitrogen containing acids.

15. The method of claim 1, wherein X is a deprotonated sulfur containing acid.

16. The method of claim 1, wherein X is a deprotonated carboxcyclic acid, except trifluro acetic acid.

17. The method of claim 1, wherein X is deprotonated phosphoric acid or any phosphorus containing acid.

18. The method of claim 1, wherein X is deprotonated tartaric acid.

19. The method of claim 1, wherein X is deprotonated perchloric acid.

20. The method of claim 1, wherein X is deprotonated p-tolulene sulfonic acid.

21. The method of claim 1, wherein X is a deprotonated picric acid.

22. The method of claim 1, wherein the formed taxane is taxol A.

23. The method of claim 1, wherein the formed taxane is taxol B.

24. The of claim 1, wherein the formed taxane is taxol C.

25. The method of claim 1, wherein the formed taxane is taxol D.

26. The method of claim 1, wherein the formed taxane is taxol E.

27. The method of claim 1, wherein the formed taxane is taxol F.

28. The method of claim 1, wherein the formed taxane is taxol G.

29. The method of claim 1, wherein the formed taxane is Docetaxel.

30. The method of claim 1, wherein the formed taxane is Nonataxel.

31. The method of claim 1, wherein the method further comprises contacting the benzoylation solution with an amine containing compound after the benzoylation reaction is complete.

32. The method of claim 31, wherein the amine containing compound comprises a primary amine.

33. The method of claim 31, wherein the amine containing compound comprises ammonium hydroxide.

34. The method of claim 31, wherein the method further comprises isolating an organic layer and washing the organic layer with a composition comprising an amine containing compound.

35. The method of claim 13, wherein the solvent used in step (iii) is selected from the group consisting of methyl tert-butyl ether, dichioromethane, heptane, hexane, toluene, and trifluorotoluene.

36. The method of claim 13, wherein the acid used in step (ii) is selected from the group consisting of sulfuric acid, nitric acid, phosphoric acid, tartaric acid, p-toluene sulfonic acid, picric acid, and combinations thereof.

* * * * *

UNITED STATES PATENT AND TRADEMARK OFFICE
CERTIFICATE OF CORRECTION

| | | |
|---|---|---|
| PATENT NO. | : 7,605,278 B2 | Page 1 of 1 |
| APPLICATION NO. | : 10/522696 | |
| DATED | : October 20, 2009 | |
| INVENTOR(S) | : Wang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 752 days.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,605,278 B2 | Page 1 of 1 |
| APPLICATION NO. | : 10/522696 | |
| DATED | : October 20, 2009 | |
| INVENTOR(S) | : Dasheng Wang et al. | |

It is certified that error appears in the above-identified patent and that said Letters Patent is hereby corrected as shown below:

In claim 9, column 16, lines 66-67, delete second occurrence of "triethylsilyl" and insert --trimethylsilyl-- therefor.

In claim 11, column 17, lines 4-5, delete second occurrence of "triethylsilyl" and insert --trimethylsilyl-- therefor.

Signed and Sealed this
First Day of November, 2011

David J. Kappos
*Director of the United States Patent and Trademark Office*